(12) United States Patent
Meyer (10) Patent No.: US 7,335,209 B2
(45) Date of Patent: Feb. 26, 2008

(54) PLUNGER NEEDLE FOR AN INTRAOCULAR LENS INJECTOR

(75) Inventor: Rolf Meyer, Port (CH)

(73) Assignees: Asico LLC, Westmont, IL (US); Anton Meyer & Co. AG, Nidau (CH)

( * ) Notice: Subject to any disclaimer, the term of this patent is extended or adjusted under 35 U.S.C. 154(b) by 498 days.

(21) Appl. No.: 10/364,504

(22) Filed: Feb. 12, 2003

(65) Prior Publication Data
US 2004/0111094 A1 Jun. 10, 2004

(30) Foreign Application Priority Data
Dec. 9, 2002 (EP) .................... 02406079

(51) Int. Cl.
*A61F 9/00* (2006.01)
(52) U.S. Cl. ..................................... 606/107
(58) Field of Classification Search ................ 606/107, 606/166; 623/4, 6, 4.1, 6.11, 5.11, 5.12
See application file for complete search history.

(56) References Cited

U.S. PATENT DOCUMENTS

| | | | |
|---|---|---|---|
| 5,643,276 A | 7/1997 | Zaleski | |
| 5,928,245 A * | 7/1999 | Wolf et al. | 606/107 |
| 6,010,510 A | 1/2000 | Brown et al. | |
| 6,022,358 A | 2/2000 | Wolf et al. | |
| 6,056,757 A * | 5/2000 | Feingold et al. | 606/107 |
| 6,074,397 A * | 6/2000 | Chambers et al. | 606/107 |
| 6,162,229 A * | 12/2000 | Feingold et al. | 606/107 |
| 6,241,737 B1 | 6/2001 | Feingold | |
| 6,447,520 B1 * | 9/2002 | Ott et al. | 606/107 |

FOREIGN PATENT DOCUMENTS

WO    WO 02/074208 A2    9/2002

* cited by examiner

*Primary Examiner*—Kevin T. Truong
(74) *Attorney, Agent, or Firm*—Rothwell, Figg, Ernst & Manbeck

(57) ABSTRACT

A plunger needle (3) for an intraocular lens injector has a plunger tip (4) with a contact area for making contact with a lens (L), the contact area being arranged in a front face (40) of the plunger tip (4), which is curved cylindrically. The plunger needle (3) according to the invention, with its specially configured plunger tip (3), permits reliable guiding of the lens (L) upon injection into an eye and prevents the lens (L) becoming stuck in the injector. It is also easy to produce.

24 Claims, 9 Drawing Sheets

PLUNGER NEEDLE FOR AN INTRAOCULAR LENS INJECTOR

TECHNICAL FIELD

The invention relates to a plunger needle for an intraocular lens injector.

PRIOR ART

Opaque natural lenses can be replaced with artificial lenses called IOLs. In this procedure, the patient's opaque lens is first removed. The artificial lens is then fitted, either manually with the aid of forceps, or using an injector. This injector consists principally of a sleeve-shaped grip body with a lens holder and with a plunger which can be displaced in a guided manner in the grip body. The lens, packed in a cartridge in the folded state, is inserted into the lens holder. In the same way as in a syringe, the lens is injected through an opening into the eye. To do so, the plunger is either pushed forward in a straight line or is turned forward in a guided manner in a thread. The lens is able to unfold in the eye, the unfolding often being assisted by rotation of the plunger.

Various injectors are known in the prior art. A list of the best known types is provided in the introductory part of the description in U.S. Pat. No. 6,010,510. Moreover, another injector is described in the as yet unpublished U.S. patent application Ser. No. 10/224,321 from the inventor.

If such injectors are used, care must be taken to ensure that the plunger can push the artificial lens through the opening without damaging it. The plunger for this reason has a plunger needle with a plunger tip which is so configured as to permit injection of the lens without any damage. In addition, measures must be taken to ensure that at no time does the lens move in an undesired way about the plunger tip and become stuck in the injector.

Inserting the lens without damage is made difficult by anchoring means, referred to as haptics, which may be present on the lens. Since these anchoring means protrude from the folded lens, they can easily become stuck between the plunger and the inner injector wall and be torn off.

The plunger needles known hitherto satisfy these conditions only partially, or can only be used in specially adapted injectors.

Thus, U.S. Pat. No. 5,643,276 and U.S. Pat. No. 6,447,520 describe plunger needles with a fork-shaped plunger tip in which the lens can be clamped.

U.S. Pat. No. 6,010,510 discloses a plunger needle with a plunger tip which is tongue-shaped. The plunger tip is in this case offset relative to the longitudinal axis of the plunger. This is intended to ensure that the plunger tip is pressed against the base of the cartridge when pushed forward. The plunger tip should therefore not be able to be pushed over the lens, so that the lens cannot move in an undesired manner about the plunger needle. However, to ensure that this is achieved, the cartridge must have a step on the inside so that the plunger tip can slide under the lens.

U.S. Pat. No. 6,241,737 shows a faceted plunger tip with a concave front face for contact with the lens. This plunger tip is relatively complex and is correspondingly difficult to produce. In addition, it has a large number of edges, which increases the risk of damaging the lens.

SUMMARY OF THE INVENTION

It is therefore an object of the invention to provide a plunger needle for an intraocular lens injector which permits safe ejection of a folded lens and avoids the latter becoming stuck inside the injector.

This object is achieved by a plunger needle with the features of claim 1.

The plunger needle according to the invention has a plunger tip whose front face, or at least its circumferential edge area forming the contact area, is curved in a cylinder shape. In other words, the front face is curved like a negative image of part of a jacket surface of a cylinder, in particular of a circular cylinder. In a side view, the front face is curved inward, this curvature being repeated in a constant manner along the axis perpendicular to this view, in the same way as in a cylinder.

This plunger needle can be produced relatively easily. In the front area, it has a minimal amount of edges, so that the lens is not damaged. In addition, it can be used in different types of injectors and for different lens types. However, the radius of curvature of the front face of the plunger tip is preferably adapted to the respective radius of the lens so that the front face bears optimally on the folded lens and can eject the latter evenly and in a guided manner from the injector. The length of the curvature, here designated by the angle of opening of the cylinder segment, is preferably adapted to the degree of folding of the lens. The curvature is preferably sufficiently long to make contact with a substantial part of the vertical height of the two branches of the folded lens. In addition, the plunger tip is wide enough to ensure that it makes contact with the two branches of the folded lens.

In a preferred embodiment, the plunger tip has an indentation for receiving a haptic of the lens, so as to prevent damage to the haptic. If, in the area behind the plunger tip, the plunger needle also has a bearing surface flush with the deepest area of this indentation, the safety is still further enhanced.

Further advantageous embodiments are evident from the dependent claims.

BRIEF DESCRIPTION OF THE DRAWINGS

The subject of the invention is explained below on the basis of preferred illustrative embodiments which are shown in the attached drawings. In these drawings:

FIG. 1a shows a perspective view of an injector;

FIG. 1b shows the injector according to FIG. 1a with a plunger needle according to the invention having been pushed through;

7d shows a view of the plunger needle according to FIG. 7a from the front;

FIG. 9a shows a side view of a plunger needle according to the invention, with a plunger tip in an eighth embodiment;

FIG. 9b shows a part of the plunger needle according to FIG. 9a in an enlarged view, and FIG. 9c shows a view of the plunger needle according to FIG. 9a from the front.

EMBODIMENTS OF THE INVENTION

Figures 1A, 1B:
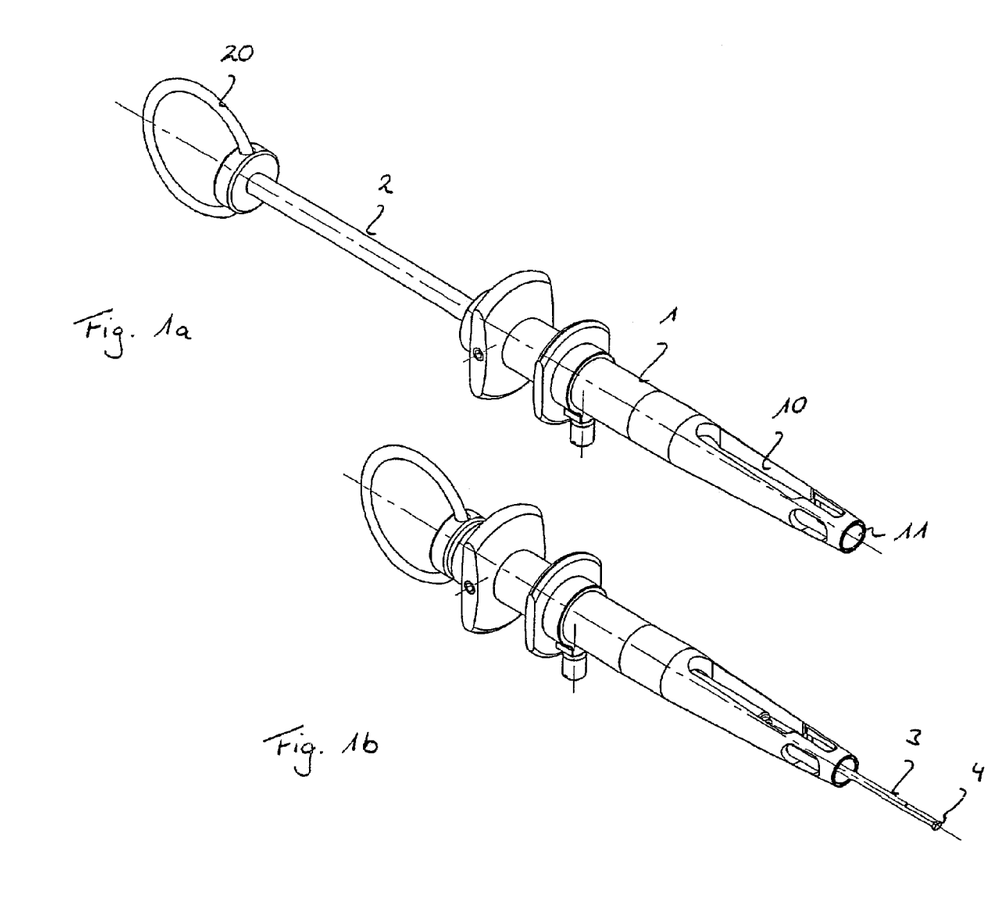

FIGS. 1a and 1b show an example of an intraocular injector. The embodiments of the plunger needle according to the invention which are described below can, however, also be used in other injectors, particularly the injectors which are standard today.

The injector has a sleeve-shaped grip body 1 through which a plunger passes. The plunger has a plunger rod 2 with a finger ring 20 arranged at its rear end, in particular for the thumb, and a plunger needle 3 arranged at its front end. The plunger needle 3 can be secured releasably on the plunger rod 2, in particular via a threaded connection.

The grip body has a lens holder 10 for receiving a lens (not shown here). The lens is usually inserted with a cartridge into the lens holder 10. The cartridge protrudes from the front end of the lens holder. The lens is pushed out of the cartridge by means of the plunger and injected into a patient's eye.

A first illustrative embodiment of a plunger needle 3 according to the invention is shown in FIGS. 2a through 2d. In these figures, and also in all the subsequent figures described, the plunger needle 3 is shown enlarged.

The plunger needle 3 is preferably made of metal, in particular titanium. Other materials can also be used, however. It tapers preferably toward its front end. In this example, it is configured in a number of stages, in this case with three stages 30, 31, 32. A plunger tip 4 is formed integrally on said front end and is axially offset relative to a longitudinal axis 33 of the plunger needle 3. The plunger tip 4 is wider than an area of the plunger needle 3 adjoining it and thus forms a shoe. This adjoining area preferably has a plane facet, which forms a bearing surface 34.

Figures 2A, 2B, 2C, 2D:
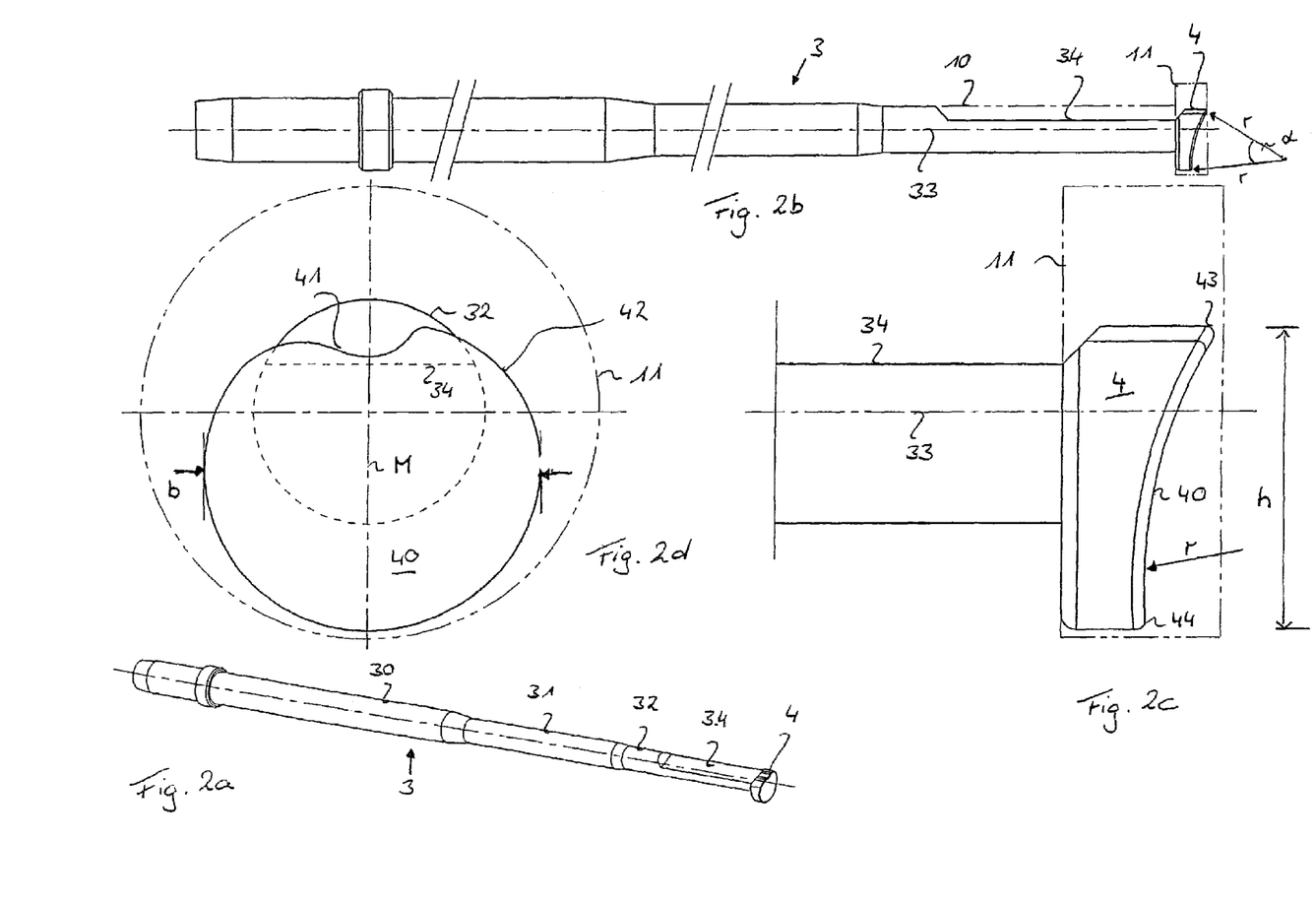
FIG. 2a shows a perspective view of a plunger needle according to the invention with a plunger tip in a first embodiment.
FIG. 2b shows the plunger needle according to FIG. 2a in a side view.
FIG. 2c shows a part of the plunger needle according to FIG. 2a in an enlarged view.
FIG. 2d shows a view of the plunger needle according to FIG. 2a from the front.

The body shown by broken lines in FIGS. 2b and 2c represents the outer grip body 1, or its front end with the lens holder 10 and the through-opening 11. As can be seen in FIG. 2b, the second stage 31 serves as a front abutment when the plunger is pushed forward.

The outermost circle shown by a broken line in FIG. 2d represents the outer contours of the frontmost tip of the grip body 1, which includes the through-opening 11.

The plunger tip 4 is preferably also made of a metal, in particular titanium. However, it can also be made of or coated with another material. At a front face 40, it has a contact area. This contact area makes contact with the folded lens and pushes the latter forward. This front face 40 is cylindrically curved. That is to say, the front tip in the side view according to FIGS. 2b and 2c is curved, but extends flat in the plane perpendicular to this drawing plane. It is also possible to correspondingly configure only the edge area, and to provide an inner, central area of the front face with another shape. The front face 40 of the plunger tip 4 thus has a first edge area 43 which protrudes farther from the plunger needle 3 than does a diametrically opposite second edge area 44. In the example shown here, this first edge area lies nearer to the longitudinal axis 33 of the plunger needle 3 than does the second edge area 44.

The radius of curvature r of the front face of the plunger tip 4 is adapted to the radius of the lens and is usually 3 mm.

The angle of opening a is usually between 21° and 39°. The maximum width b is usually 1.6-2.2 mm. The angle of opening a, ie, the angle between normal vectors at opposite ends of the contact area, and the maximum width b take into account the degree of folding of the lens. The maximum height h is usually 1.7-2.2 mm. However, it is also possible for the front face 40 to be configured with a curvature which is not circularly cylindrical but instead generally cylindrical, for example with an elliptic cylinder face.

As can be seen in FIGS. 2a and 2d, the plunger tip 4 has a jacket surface 42 which has an indentation 41. The indentation 41 is arranged at the first edge area 43 and is asymmetrically shaped in relation to an axial mid-plane M. This indentation 41 serves to receive at least one haptic, preferably exactly one haptic, of the lens. This haptic can also rest on the bearing surface 34 of the plunger needle 3 so that it cannot become entangled between plunger needle 3 and the inner wall of the grip body 1. The lowermost area of the indentation 41 is therefore preferably flush with the bearing surface 34. In the illustrative embodiment shown here, however, the bearing face 34 lies slightly deeper than the indentation 41, as can be seen in FIG. 2d.

Figure 3A:
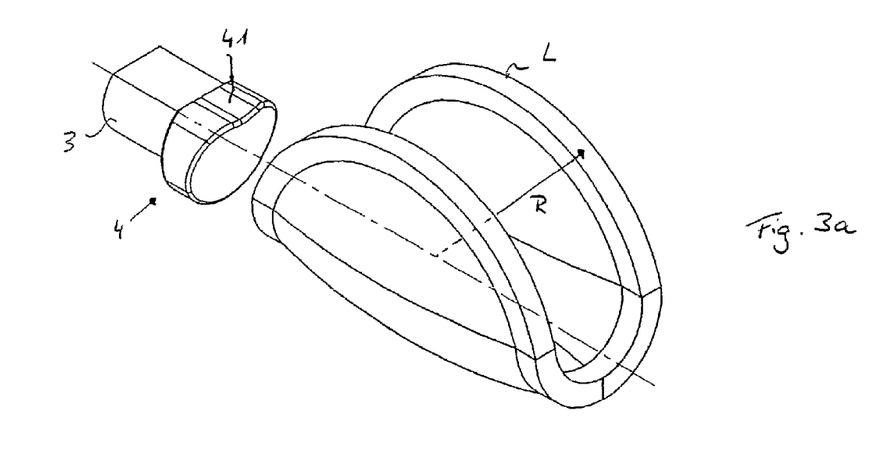
FIG. 3a shows a perspective view of the front area of a plunger needle according to the invention in a second embodiment, together with a folded lens.
Figure 3B:
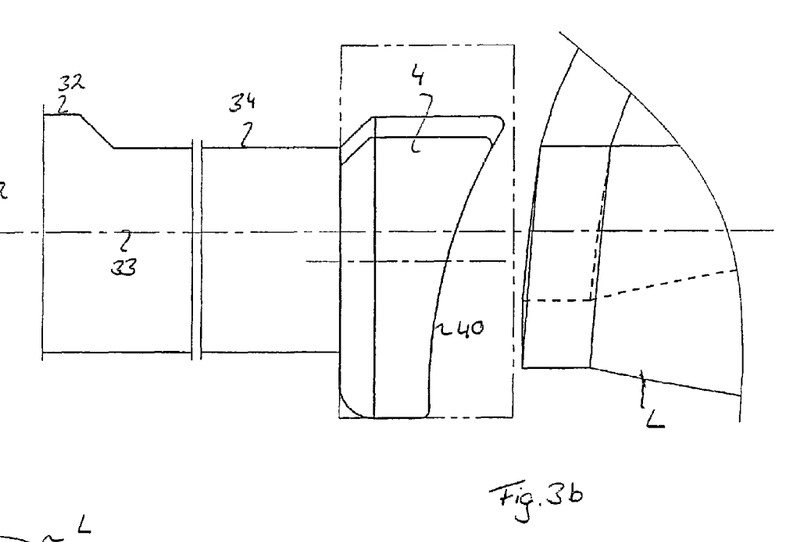
FIG. 3b shows the plunger needle according to FIG. 3a in an enlarged side view.
Figure 3C:
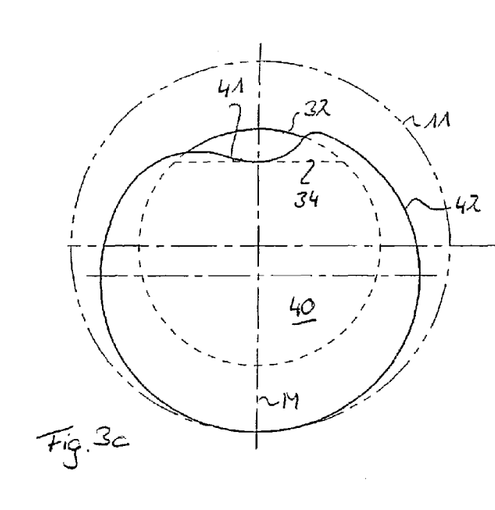
FIG. 3c shows a view of the plunger needle according to FIG. 3a from the front.
Figures 4A, 4B, 4C:
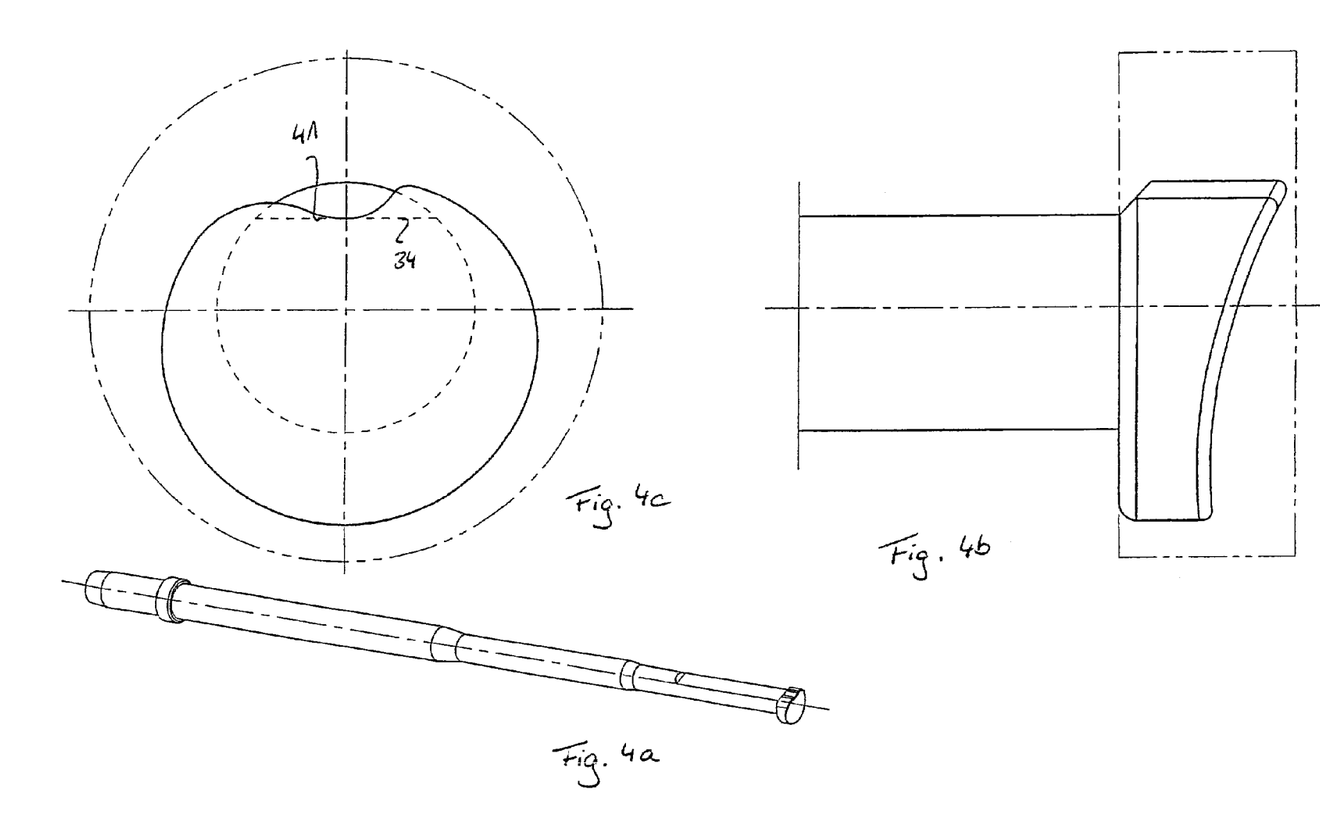
FIG. 4a shows a side view of a plunger needle according to the invention, with a plunger tip in a third embodiment.
FIG. 4b shows a part of the plunger needle according to FIG. 4a in an enlarged view.
FIG. 4c shows a view of the plunger needle according to FIG. 4a from the front.
Figure 5A:
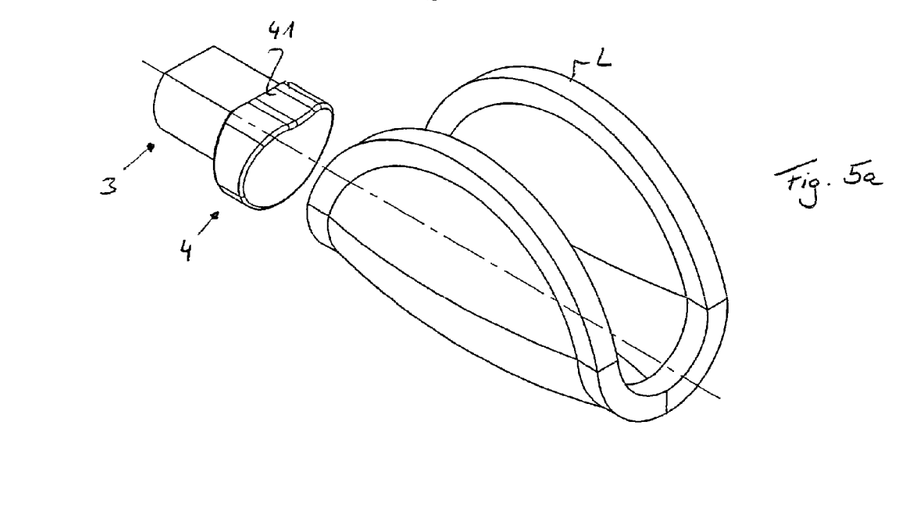
FIG. 5a shows a side view of a plunger needle according to the invention, with a plunger tip in a fourth embodiment.
Figure 5B:
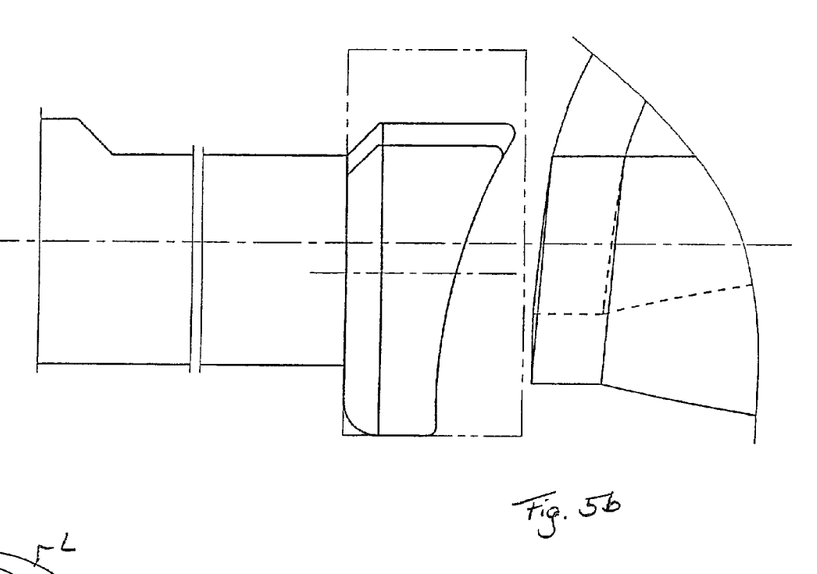
FIG. 5b shows a part of a plunger needle according to FIG. 5a in an enlarged view.
Figure 5C:
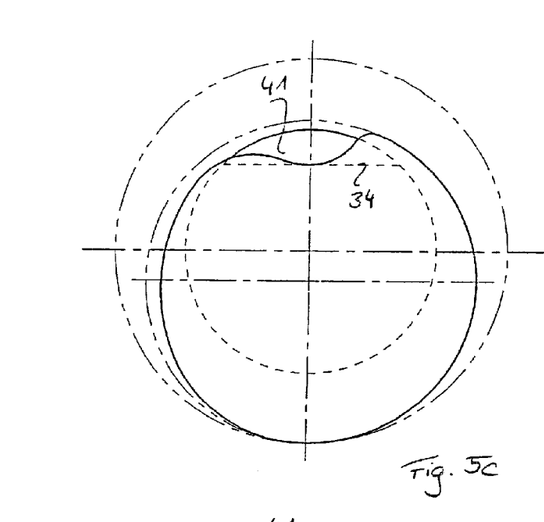
FIG. 5c shows a view of the plunger needle according to FIG. 5a from the front.
Figures 6A, 6B, 6C, 6D:
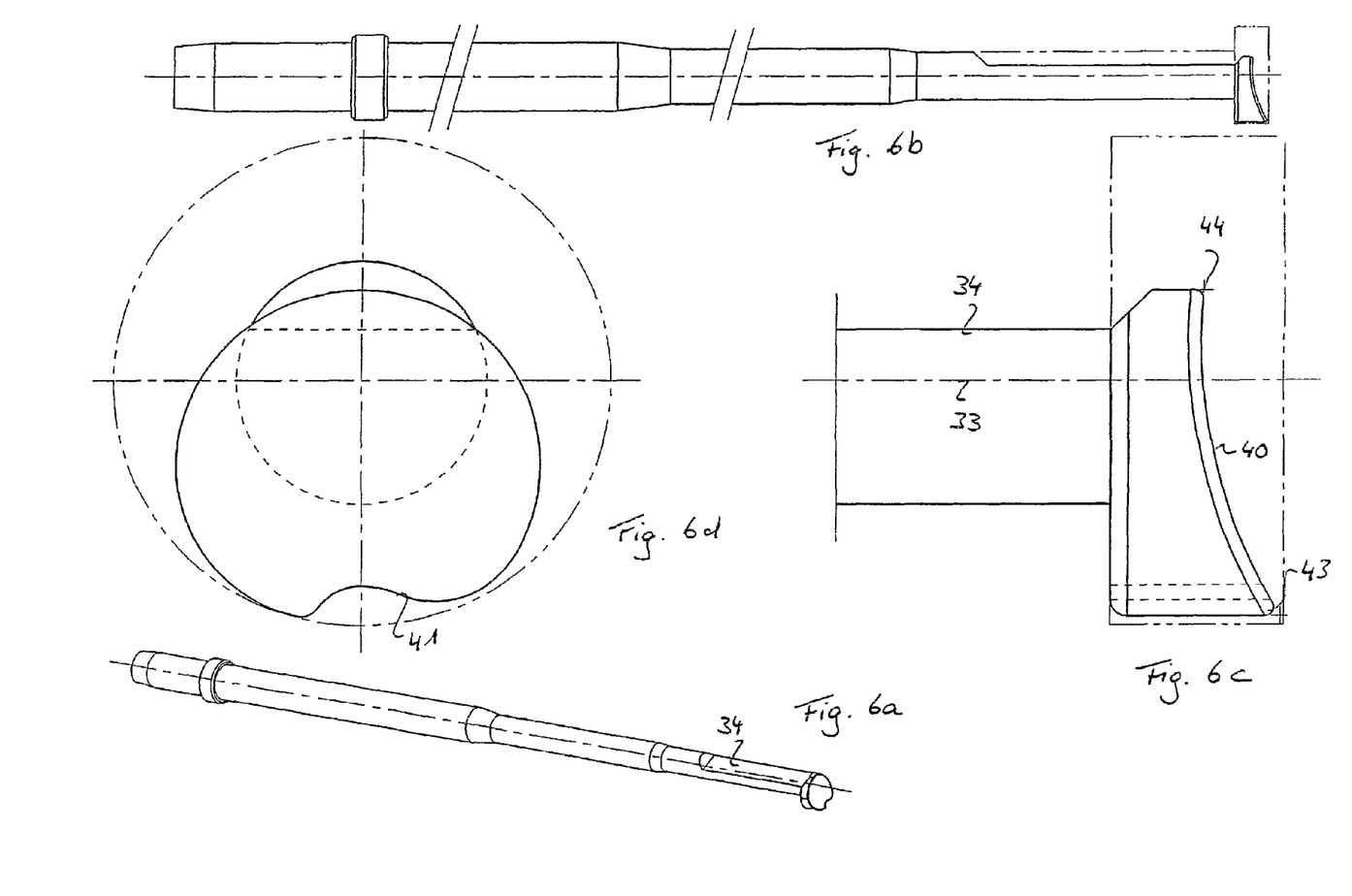
FIG. 6a shows a perspective view of a plunger needle according to the invention, with a plunger tip in a fifth embodiment.
FIG. 6b shows the plunger needle according to FIG. 6a in a side view.
FIG. 6c shows a part of the plunger needle according to FIG. 6a in an enlarged view.
FIG. 6d shows a view of the plunger needle according to FIG. 6a from the front.
Figure 7A:
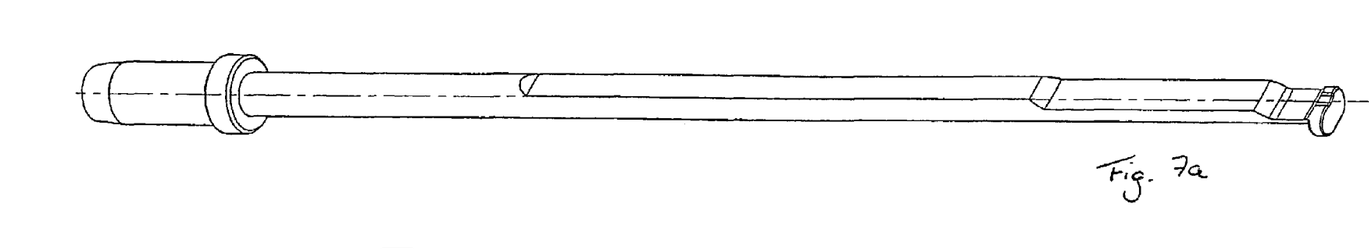
FIG. 7a shows a perspective view of a plunger needle according to the invention, with a plunger tip in a sixth embodiment.
Figure 7B:
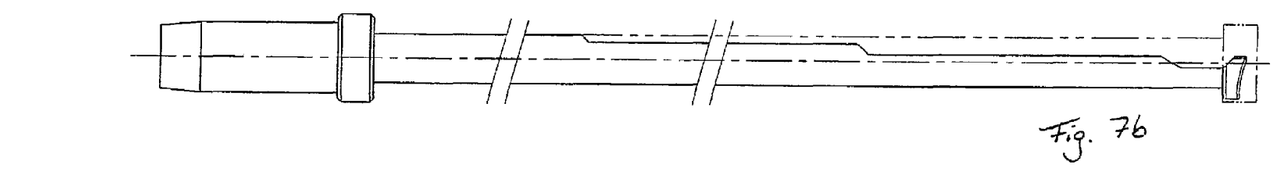
FIG. 7b shows the plunger needle according to FIG. 7a in a side view.
Figure 7C:
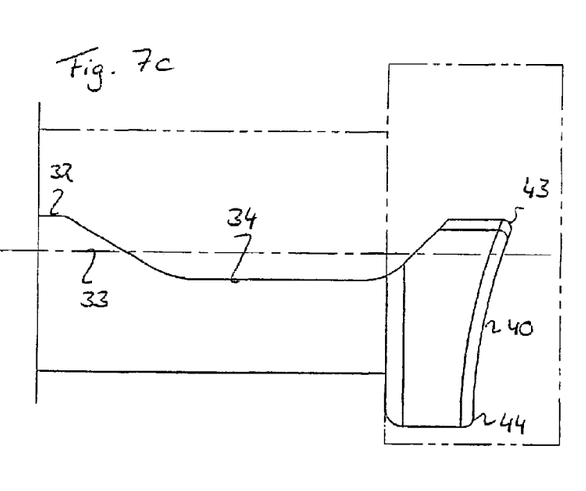
FIG. 7c shows a part of the plunger needle according to FIG. 7a in an enlarged view.
Figure 7D:
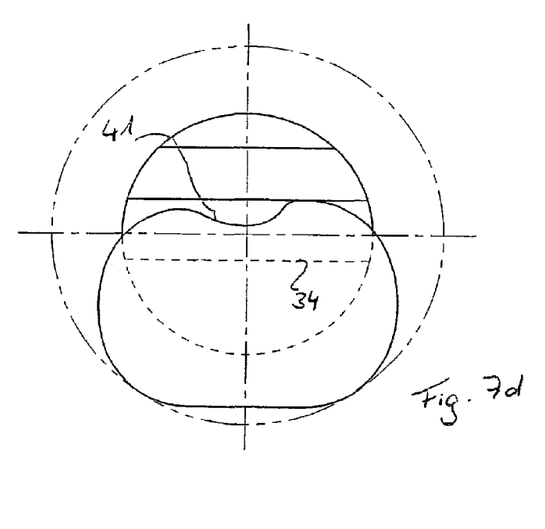

A second embodiment is shown in FIGS. 3a through 3c. Before discussing these, it should be noted that the folded lens L is now shown here in relation to the plunger tip 4. As can be seen in particular in FIG. 3b, the radius of curvature r of the front face 40 of the plunger tip 4 corresponds at least approximately to the radius R of the lens L. This ensures optimum bearing.

These lens radii R can vary depending on the manufacturing company and the lens type. In addition, the haptics are differently configured. A specific lens type is often recommended for a specific injector. In order to achieve optimum results, the radius of curvature r and the angle of opening α of the plunger tip 4 and preferably also the shape of the indentation 41 are correspondingly adapted. Likewise, the cartridges used may have another form depending on the injector and the lens type. For this reason, the plunger tip 4 is correspondingly optimized by being designed slightly differently according to the cartridge type. Thus, depending on the cartridge type and the injector type, it deviates to a slight extent from the circular basic shape of its circumference line, and the position and shape of its indentation 41 are accordingly adapted.

The subsequent figures show further illustrative embodiments which are each adapted to standard injectors, lenses and cartridges. The illustrative embodiments indicated in these and subsequent figures preferably have similar dimensions to the first illustrative embodiment.

In the embodiment according to FIGS. 6a through 6d, the first edge area 43 is farther away from the longitudinal axis 33 than the second edge area 44. The indent 41 is nevertheless arranged in the first edge area 43. The bearing surface 34 provides for better guiding through the cartridge.

Figure 8A:
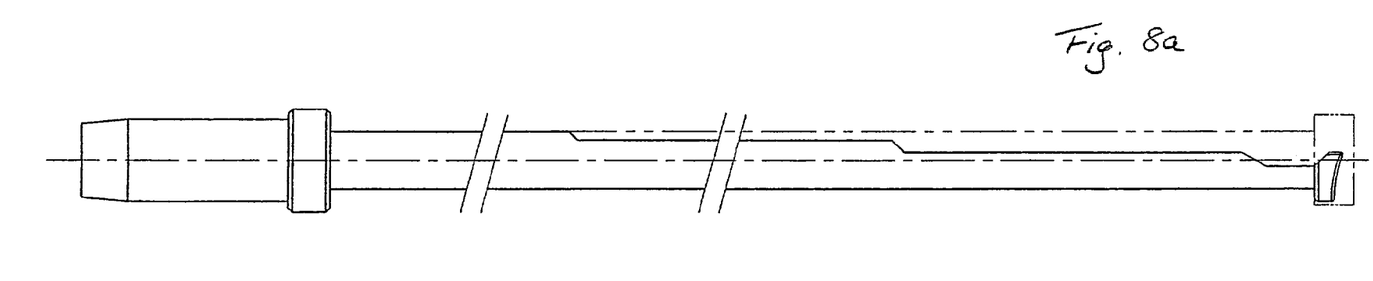
FIG. 8a shows a side view of a plunger needle according to the invention, with a plunger tip in a seventh embodiment.
Figure 8B:
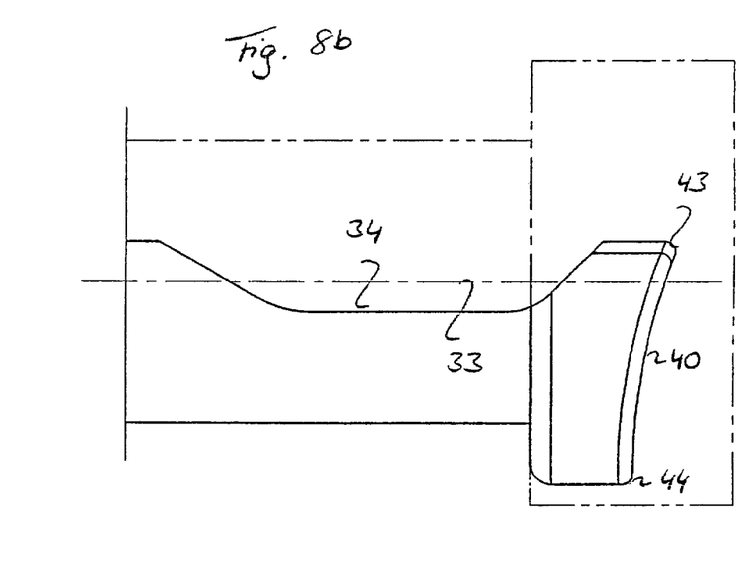
FIG. 8b shows a part of the plunger needle according to FIG. 8a in an enlarged view.
Figure 8C:
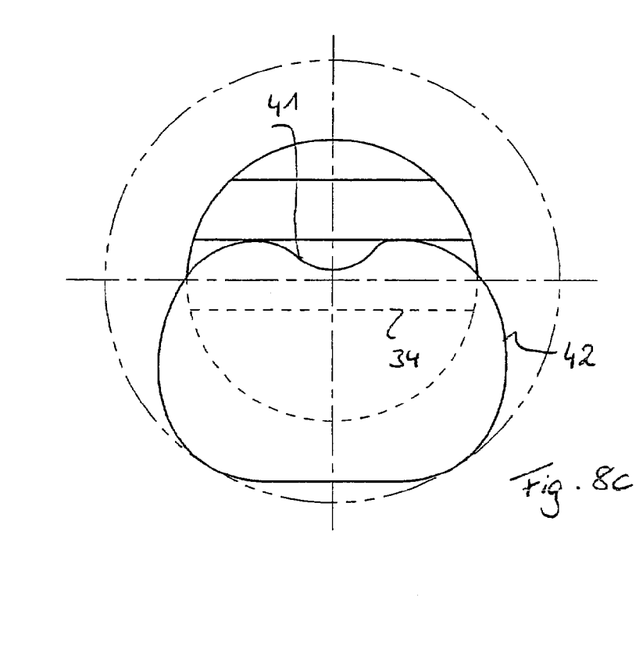
FIG. 8c shows a view of the plunger needle according to FIG. 8a from the front.

In the embodiments according to FIGS. 7a through 7d and 9a through 9c, the plunger tip 4 has a somewhat flattened circular or elliptic basic shape. In the illustrative embodiment according to FIGS. 8a through 8c, the indentation 41 is designed at least approximately symmetrically with respect to the mid-plane M and the basic shape is again a somewhat flattened circle. In these illustrative embodiments, the plunger needle also has three flattened facets. The first facet, which again forms the bearing surface 34, lies substantially deeper than the lowermost area of the indentation 41.

The plunger needle 3 according to the invention, with its specially shaped plunger tip 4, permits reliable guiding of the lens L during injection into an eye and prevents the lens becoming stuck in the injector. In addition, it is easy to produce.

LIST OF REFERENCE NUMBERS

1 grip body
10 lens holder
11 through-opening
2 plunger rod
20 finger ring
3 plunger needle
30 first stage
31 second stage
32 third stage
33 longitudinal axis
34 support surface
4 plunger tip
40 front face
41 indentation
42 jacket surface
43 first end area
44 second end area
r radius of curvature of front face of plunger tip
α angle of opening
b maximum width
h maximum height
L lens R
R radius of curvature of the lens
M axial mid-plane The iuvention claimed is:

1. A plunger needle for use with an intraocular lens injector, the plunger needle comprising:
    a plunger tip having a contact area for making contact with the lens and for pushing the intraocular lens through an opening in the intraocular lens injector for insertion into an eye, the contact area being arranged in a front face of the plunger tip,
    wherein at least the contact area of the front face is inwardly curved, and
    wherein the plunger needle has a longitudinal axis, and wherein the plunger tip is arranged axially offset relative to this longitudinal axis.

2. The plunger needle as claimed in claim 1, wherein the plunger tip is wider than an adjacent area of the plunger needle.

3. The plunger needle as claimed in claim 1, wherein said plunger needle is adapted for being releasably secured to a plunger rod.

4. The plunger needle as claimed in claim 1, wherein said contact area is curved like the negative image of a jacket surface of a cylinder.

5. The plunger needle as claimed in claim 1, wherein the plunger tip is arranged axially offset relative to the longitudinal axis along an offset direction, and wherein said contact area has an axis of curvature which is perpendicular both to said longitudinal axis and to the offset direction of the plunger tip.

6. The plunger needle as claimed in claim 5, wherein said axis of curvature is offset relative to said longitudinal axis.

7. The plunger needle as claimed in claim 1, wherein the front face of the plunger tip, in a first edge area, protrudes farther from the plunger needle than at a diametrically opposite second edge area.

8. The plunger needle as claimed in claim 7, wherein the first edge area is the edge area which lies nearer the longitudinal axis than the second edge area, or wherein the first edge area is the edge area arranged farther away from the longitudinal axis than the second edge area.

9. The plunger needle as claimed in claim 1, wherein the plunger tip has a jacket surface with an indentation for receiving at least one haptic of the lens.

10. The plunger needle as claimed in claim 9, wherein the front face of the plunger tip, at a first edge area, protrudes farther from the plunger needle than at a diametrically opposite second edge area, and wherein the indentation is arranged at the first edge area.

11. The plunger needle as claimed in claim 9, wherein the plunger tip is arranged axially offset relative to the longitudinal axis along an offset axis, said offset axis being perpendicular to said longitudinal axis, and wherein said indentation is arranged centrally with respect to said offset axis.

12. The plunger needle as claimed in claim 9, wherein the plunger needle has a bearing surface in an area behind the plunger tip, and wherein the indentation in its deepest area is flush with the bearing surface.

13. An injector for inserting an intraocular lens into an eye, comprising:
    a grip body; and
    a plunger displaceable in said grip body in a guided manner, said plunger comprising a plunger needle including a plunger tip having a contact area for making contact with the lens, the contact area being arranged in a front face of the plunger tip,
    wherein at least the contact area of the front face is inwardly curved, and wherein the plunger needle has a longitudinal axis, and wherein the plunger tip is arranged axially offset relative to this longitudinal axis.

14. The injector as claimed in claim 13, wherein said contact area is curved like the negative image of a jacket surface of a cylinder.

15. The injector as claimed in claim 13, said plunger further comprising a plunger rod, and said plunger needle being releasably secured to said plunger rod.

16. The injector as claimed in claim 13, further comprising a lens holder on said grip body and a cartridge disposed in said lens holder, said plunger needle passing through said cartridge for pushing said lens out of said cartridge.

17. The injector as claimed in claim 16, wherein the plunger tip has a substantially circle-shaped circumference line, with deviations from the circle shape being adapted to the type of cartridge used.

18. A plunger needle for use with an intraocular lens injector, the plunger needle comprising:
a longitudinal axis, and
a plunger tip having a contact area for making contact with the lens and for pushing the intraocular lens through an opening in the intraocular lens injector for insertion into an eye, the contact area being arranged in a front face of the plunger tip,
wherein at least the contact area of the front face is inwardly curved,
wherein the contact area has an axis of curvature that is perpendicular to said longitudinal axis, and
wherein the contact area has an angle of opening, defined as the angle between normal vectors at opposing ends of the contact area, of 21° to 39°.

19. The plunger needle as claimed in claim 18, wherein said contact area is curved like the negative image of a jacket surface of a cylinder.

20. The plunger needle as claimed in claim 18, wherein the contact area has a radius of curvature of approximately 3 millimeters.

21. An injector for inserting an intraocular lens into an eye, comprising:
a grip body; and
a plunger displaceable in said grip body in a guided manner, said plunger comprising a plunger needle including a longitudinal axis and a plunger tip, the plunger tip having a contact area for making contact with the lens and for pushing the intraocular lens through an opening in the intraocular lens injector for insertion into an eye, the contact area being arranged in a front face of the plunger tip,
wherein at least the contact area of the front face is inwardly curved,
wherein the contact area has an axis of curvature that is perpendicular to said longitudinal axis, and
wherein the contact area has an angle of opening, defined as the angle between normal vectors at opposing ends of the contact area, of 21° to 39°.

22. The injector as claimed in claim 21, wherein said contact area is curved like the negative image of a jacket surface of a cylinder.

23. The injector as claimed in claim 21, wherein the contact area has a radius of curvature of approximately 3 millimeters.

24. The injector as claimed in claim 21, in which the injector can be assigned at least one type of lens for use with this injector, and this type of lens has a radius of curvature, wherein the radius of curvature of the contact area of the plunger tip corresponds at least approximately to this radius of curvature of the lens.

* * * * *